United States Patent [19]

Chang

[11] Patent Number: 5,290,702
[45] Date of Patent: Mar. 1, 1994

[54] METHOD OF DETECTING AND MAPPING ORGANIC SOLVENT-CONTAINING MATERIALS ON A SURFACE

[75] Inventor: On-Kok Chang, San Jose, Calif.

[73] Assignee: Valence Technology, Inc., San Jose, Calif.

[21] Appl. No.: 35,336

[22] Filed: Mar. 19, 1993

[51] Int. Cl.$^5$ .................... G01N 31/22; G01N 33/98
[52] U.S. Cl. ............................... 436/2; 436/3; 436/5; 436/74; 436/92; 436/98; 436/127; 436/128; 436/130; 436/131; 436/132
[58] Field of Search ............... 436/2, 3, 5, 98, 127, 436/128, 130, 131, 132, 74, 92

[56] References Cited

U.S. PATENT DOCUMENTS

| | | | |
|---|---|---|---|
| 3,955,926 | 5/1976 | Fischer | 436/92 |
| 4,277,248 | 7/1981 | Osadca | 436/98 |
| 4,786,629 | 11/1988 | Kawakami et al. | 503/200 |
| 4,847,066 | 7/1989 | Honigs et al. | 436/2 |
| 4,855,282 | 8/1989 | Satomura et al. | 503/218 |
| 4,992,381 | 2/1991 | Cran et al. | 436/74 |
| 5,053,339 | 10/1991 | Patel | 436/2 |
| 5,151,403 | 9/1992 | Suzuki et al. | 503/200 |

*Primary Examiner*—James C. Housel
*Assistant Examiner*—Rachel Heather Freed
*Attorney, Agent, or Firm*—S. Russell LaPaglia

[57] ABSTRACT

Chromogenic solvent detectors are used to detect and map the presence of organic solvent-containing materials on a surface. The detector need only be applied to the surface to be tested. When removed, the dark areas on the detector correspond to those areas of the surface where an organic solvent-containing material was present. This method can be used to test the release properties of a release film.

19 Claims, No Drawings

METHOD OF DETECTING AND MAPPING ORGANIC SOLVENT-CONTAINING MATERIALS ON A SURFACE

FIELD OF THE INVENTION

The present invention relates to a method for detecting organic solvent-containing materials on a surface. More specifically, the present invention relates to a method for detecting and mapping organic solvent-containing materials by contacting, either directly or indirectly, the surface suspected of having the organic solvent-containing material with a chromogenic solvent detector and analyzing the detector for discoloration caused by the organic solvent-containing material.

BACKGROUND OF THE INVENTION

Chromogenic record materials are well known in the art and are described in a number of patents, for example, U.S. Pat. Nos. 3,539,375; 3,674,535; 3,746,675; 4,151,748; 4,181,771; 4,246,318 and 4,470,057 which are incorporated herein by reference. In these systems, basic chromogenic material and acidic developer material are contained in a coating on a substrate which, when heated to a suitable temperature, melts or softens to permit the materials to react, thereby producing a colored mark. The use of solvents to induce chromogenic markings for mapping the solvents' presence on a surface would be highly desirable.

A method for quickly and easily detecting and mapping the presence of organic solvent-containing materials on a surface would be advantageously used in many applications in the manufacturing arts. A method for detecting and mapping the presence of organic solvent-containing materials on surfaces having different shapes and contours would be especially useful. A particular application would be to provide a quick and easy method of testing the release properties of a release material by using a chromogenic solvent detector.

SUMMARY OF THE INVENTION

Accordingly, there is provided a method for detecting and mapping the presence of organic solvent-containing materials on a surface. The method comprises contacting a surface which is suspected of having or is known to have an organic solvent-containing material with a chromogenic solvent detector. In a preferred embodiment, the organic solvent on the surface is transferred to the detector by means of an inert transfer means. The detector is then analyzed for discolorations caused by the organic solvent-containing material.

Accordingly the present invention provides a chromogenic organic solvent detector made of a substrate, a binder means which is substantially soluble to the organic solvent, an electron donating chromogenic composition dispersed on the substrate in connection with the binder means, and an electron accepting composition, which forms a color with the chromogenic composition, dispersed on the substrate in connection with the binder means. The present invention includes a method of making the described detector, including the step of selecting a binder means which is substantially soluble to one solvent to be detected. Preferably, the binder means is selectively substantially soluble to the solvent, or the class of compounds to which the solvent belongs.

Also provided according to the present invention is a method of testing the release properties of a release material. The method comprises contacting a surface which was previously in contact with an organic solvent-containing material with a chromogenic organic solvent detector and then detecting and mapping the presence of any organic solvent-containing material adhered to the surface of the release material by analyzing the detector for discolorations caused by the organic solvent-containing material.

DESCRIPTION OF THE PREFERRED EMBODIMENTS

The term "contact" is intended to include both the direct contact of a chromogenic organic solvent detector to a surface containing an organic solvent-containing material as well as the indirect contact of the detector to a surface containing an organic solvent-containing material by, e.g., indirectly transferring the organic solvent-containing material to the detector via an inert transfer means.

The term "release material" is intended to include any type of material which is designed to be applied to a solid or liquid surface and to be withdrawn again from that surface without withdrawing the surface material to which it was applied. Examples of such materials include, e.g., Mylar, polyester film polypropylene, silicone-based materials, etc.

The term "extraneous materials" is intended to include those materials, primarily liquids, for which detection and mapping are not desired, i.e., any materials other than the organic solvent-containing material which is to be detected and mapped.

The present invention represents a quick and effective method of detecting and mapping organic solvent-containing materials on a surface. The present method is capable of effectively detecting and mapping organic solvent-containing materials over a vast array of surfaces having a wide range of contours. For example, a chromogenic organic vapor detector can be wrapped around a rounded contour such as a pipe or bent to mold itself into a corner. However, the present method is most easily employed in detecting and/or mapping organic solvent-containing materials on flat, relatively smooth surfaces.

According to the method of the invention, the surface which is to be tested is contacted with the detector. In this regard, the detector may be contacted directly to the surface or an inert transfer means may be employed to indirectly transfer the organic solvent-containing material to the detector. Where sensitivity is an issue, it is preferred to apply the detector directly to the surface to be tested.

However, on surfaces where extraneous liquids are present, i.e., liquids which are not being tested for, it is preferred to indirectly transfer the organic solvent-containing material to an inert transfer means. For example, the inert material may comprise a filter paper or the like which is applied to the surface to be tested and/or mapped. Once the organic solvent-containing material has been transferred to the filter paper, it can then be transferer to the detector. One advantage of using an inert transfer material such as filter paper is that the filter paper may be used to screen out extraneous liquids by either absorbing the extraneous liquids and/or allowing the extraneous liquids to air dry before transferring the organic solvent-containing material from the filter paper to the detector.

Another variation of this method employs the use of at least two inert transfer means. For example, one inert transfer means may be a filter paper as described above and the second inert transfer means may be a microporous separator sheet such as Celgard TM microporous polypropylene or the like. In this type of variation, the first inert means is in direct contact with the surface to be tested so as to transfer the organic solvent-containing material from the surface to the first inert transfer means. The second inert transfer means may be used to pull away and absorb extraneous liquids. In this way, the second inert transfer means acts to reduce the interference of the detection and mapping processes caused by extraneous liquids. That is, the first inert transfer means may then transfer the organic solvent-containing material to the detector for detection and mapping without the interference of extraneous liquids that may also be present on the surface.

The method of the present invention is effective in detecting a vast array of organic solvents and/or organic solvent-containing materials. It is preferred, however, that the organic solvent is a polar solvent, i.e., one having a dielectric constant of greater than about 8, and preferably greater than about 12, and more preferably greater than about 16 The present method is also useful in detecting substantially all heteroatom-containing solvents.

Several examples of preferred polar solvents and heteroatom-containing solvents include the following: alcohols such as methanol, ethanol, propanol, isopropanol, butanol, etc.; ketones; esters; acetone; dimethylsulfoxide; dioxolanes; sulfolanes; butyrolactones; tetrahydrofurans; ethers such as glyme, diglyme, triglyme, tetraglyme, octaglyme, etc.; and alkyl carbonates such as propylene carbonate and the like. The invention is also applicable to a number of additional solvents not specifically enumerated above. The method of the invention is also capable of detecting a wide range of organic solvent-containing materials. One such example is electrolytes such as those used in manufacturing electrolytic cells, e.g., solid batteries.

Typically, the chromogenic organic solvent detector comprises a substrate, an electron donating color former, also referred to as chromogenic compounds, electron donating dye precursors, non-polymeric colorless dyes, etc., an electron accepting (acidic) co-reactant, and a binder means. The chromogenic compound and the electron accepting composition, which forms a color with said chromogenic compound, are dispersed on said substrate in connection with the binder means.

In general, the binder means is selected to be soluble to an organic solvent whose presence it is desired to detect. However, the binder means will normally be soluble to a whole class of organic solvents.

The binder means performs several functions. Primarily, the binder means serves to improve the adhesion of the chromogenic composition and the developer (electron accepting composition) to the substrate. The binder means can also serve to protect the dispersed compositions from brushing and handling forces. So-called thermal papers also contain a waxy substance which is selected to melt at a prescribed temperature. Binders also encompass the microencapsulation of the color-forming compositions of this invention. Most importantly, in the practice of this invention, the binder means serves as a means of keeping the color-forming compositions apart until the binder-means is solubilized by the organic solvent. The binder means may consist of 3 or more separate and distinct compositions or materials to perform these and other functions disclosed in the art. But taken in its entirety, the functions and the o compositions or materials chosen to perform those functions are herein referred to as the binder-means. Binder means are disclosed in U.S. Pat. Nos. 4,855,282; 5,151,403; 4,470,057; 4,786,629; 4,586,061; 4,794,102; 4,535,347; 4,688,059; 4,403,791; 4,601,588 the disclosures of each are herein incorporated by reference as if fully stated in ipsis verbis. Binder means for the purposes of this invention encompasses all of the foregoing, and such portions of these compositions and materials as are necessary to permit organic solvent detection according to the present method.

Suitable binders which can be used include water-soluble high molecular weight substances and water-insoluble binders, which are used alone or in combination. Suitable water-soluble high molecular weight substances include methylcellulose, carboxymethylcellulose, hydroxyethyl cellulose, starches, gelatin, gum arabic, casein, hydrolysis products of copolymers of styrene and maleic anhydride, hydrolysis products of copolymers of ethylene and maleic anhydride, hydrolysis products of copolymers of isobutylene and maleic anhydride, polyvinyl alcohol, carboxy modified polyvinyl alcohol and polyacrylamide. Suitable water insoluble binders include generally synthetic rubber latexes and synthetic resin emulsions, such as styrene and butadiene rubber latex, acrylonitrile and butadiene rubber latex, methyl acrylate and butadiene rubber latex or a vinyl acetate emulsion.

The additive amount of binders is from 3 to 100%, preferably from 5 to 50% based on the weight of the pigments. Wax, fade preventing agents and surface active agents can be added to the binder means, if desired.

Eligible chromogenic compounds, such as the phthalide, leucauramine and fluoran compounds, for use in the color-forming system are well known color-forming compounds. Examples of suitable color-forming compounds include Crystal Violet Lactone (3,3-bis(4-dimethylaminophenyl)-6-dimethylaminophthalide, U.S. Re. Pat. No. 23,024); phenyl-, indol-, pyrrol-, and carbazol-substituted phthalides (for example, in U.S. Pat. Nos. 3,491,111; 3,491,112; 3,491,116; 3,509,174); nitro-, amino-, amido-, sulfon amido-, aminobenzylidene-, halo-, anilino-substituted fluorans (for example, in U.S. Pat. Nos. 3,624,107; 3,627,787; 3,641,011; 3,642,828; 3,681,390); spirodipyrans (U.S. Pat. No. 3,971,808); and pyridine and pyrazine compounds (for example, in U.S. Pat. Nos. 3,775,424 and 3,853,869). Other specifically eligible chromogenic compounds, not limiting the invention in any way, are: 3-diethylamino-6-methyl-7-anilino-fluoran (U.S. Pat. Nos. 3,681,390); 7-(1-ethyl-2-methylindol-3-yl)-7-(4-diethylamino-2-ethoxyphenyl)-5,7-dihydrofuro[3,4-b]pyridin-5-one (U.S. Pat. No. 4,246,318); 3-diethylamino-7-(2-chloroanilino)fluoran (U.S. Pat. No. 3,920,510); 3-(N-methylcyclohexylamino)-6-methyl-7-anilinofluoran (U.S. Pat. No. 3,959,571); 7-(1-octyl-2-methylindol-3-yl)-7-(4-diethylamino-2-ethoxyphenyl)-5,7-dihydrofuro[3,4-b]-pyridin-5-one; 3-diethylamino-7,8-benzofluoran; 3,3-bis(1-ethyl-2-methylindol-3-yl)phthalide; 3-diethylamino-7-anilinofluoran: 3-diethylamino-7-benzylaminofluoran; and 3'-phenyl-7-dibenzylamino-2,2'-spiro-di-[2H-1-benzopyran].

The electron-accepting compound which forms a color on contact with the electron-donating colorless dye polymer can be any of the conventional developer compounds known to be capable of color formation, as described in U.S. Pat. Nos, 3,491,111, 3,491,112, 3,491,116, 3,509,174, 3,624,107, 3,627,787, 3,641,011, 3,462,828, 3,681,390, 3,920,510, 3,959,571, 3,971,808, 3,775,424, 3,853,869, 4,246,318, 4,480,052, and 4,436,920, British Pat. Nos. 2,140,449, 1,018,793, 2,166,882, 2,165,953, 2,162,650, 2,156,535, and 2,154,014, Japanese Patent Publication No. 23922/85, and Japanese Patent Application (OPI) Nos. 179836/82, 123556/85, and 123557/85. Examples of the electron-accepting compound include phenol derivatives, salicyclic acid derivatives, metal salts of aromatic carboxylic acids, and acid clay.

Specific examples of the electron-accepting compound include organic developers such as 4-tertiary butyl phenol; 4-phenylphenol; 2,2-bis(4-hydroxyphenyl)propane (i.e., bisphenol A); 4,4′-isopropylidene-bis(2-methylphenol); 1,1-bis(3-chloro-4-hydroxyphenyl)cyclohexane; 1,1-bis(3-chloro-4-hydroxyphenyl)-2-ethyl butane; 4,4′-secondary isooctylidene diphenol; 4-tert-octyl phenol; 4,4′-secbutylidene diphenol; 4-chlorophenylphenol; 4,4′-isopentylidene diphenol; 4,4′-methylcyclohexylidene diphenol; 4,4′-dihydroxydiphenyl sulfide; 1,4-bis-4′-hydroxycumyl benzene; 1,3-bis-4′-hydroxycumyl benzene; 4,4′-thiobis(6-tert-butyl-3-methyl phenol); 4,4′-dihydroxydiphenyl sulfone; hydroquinone monobenzyl ether; 4-hydroxybenzophenone; 2,4-dihydroxybenzophenone; polyvinyl benzyloxycarbonyl phenol; 2,2′,4,4′-tetrahydroxybenzophenone; dimethyl 4-hydroxylphthalate; methyl 4-hydroxybenzoate; 2,4,4′-trihydroxydiphenyl sulfone; 1,5-bis-p-hydroxyphenyl pentane; 4-hydroxybenzoic α-phenylbenzyl ester; phenylpropyl 4-hydroxybenzoate; phenethyl 4-hydroxybenzoate; p-chlorobenzyl 4-hydroxybenzoate; p-methoxybenzyl 4-hydroxybenzoate; 4-hydroxybenzoic benzyl ester; 4-hydroxy-2′,4′-dimethyldiphenyl sulfone; β-phenethylorsellinate; cinnamyl orsellinate; orsellinic-o-chlorophenoxyethyl ester; o-ethylphenoxyethyl orsellinate; o-phenylphenoxyethyl orsellinate; 2,4-dihydroxybenzoic-β-3′-t-butyl-4′-hydroxyphenoxyethyl ester; stearyl gallate; 4-N-benzylsulfamoyl phenol; 2,4-dihydroxybenzoic-β-phenoxyethyl ester; 2,4-dihydroxy-6-methylbenzoic benzyl ester; allyl bis-4-hydroxyphenyl acetate; ditolyl thiourea; 4,4′-diacetyldiphenyl thiourea; 3-phenyl salicylic acid; orsellinic-β-p-methoxyphenoxyethoxyethyl ether; orsellinicβ-o-methoxyphenoxyethyl ether; orsellinic trioxyethyl ester: orsellinic-β-p-methoxyphenoxypropyl ester; β-resorcylic phenoxyethyl ether; β-resorcylic-δ-p-methoxyphenoxybutyl ester; phenylphenol-formaldehyde resin; and p-butylphenolacetylene resin; polyvalent metal salts formed of these organic developers with zinc, magnesium, aluminum, and calcium; and inorganic developers such as acid clay, activated clay, attapulgite, aluminum silicate, magnesium silicate, zinc rhodanate and complexes thereof, and zinc chloride.

Two or more of the developers enumerated above may be used in combination. Any of these developers may be used in combination with one or more members selected from at least the following inorganic developers such as iron stearate, cobalt naphthenate, nickel peroxide, and ammonium sulfate; aliphatic carboxylic acids such as oxalic acid, maleic acid, tartaric acid, citric acid, succinic acid, and stearic acid; and other organic acids such as benzoic acid, para-tertiary butylbenzoic acid, phthalic acid, or gallic acid.

Examples of eligible acidic developer material include the compounds listed in U.S. Pat. No. 3,539,375 as phenolic reactive material, particularly the monophenols and diphenols. Eligible acidic developer material also includes, without being considered as limiting, the following compounds which may be used individually or in mixtures: 4,4′-isopropylidinediphenol (Bisphenol A); p-hydroxybenzaldehyde; p-ydroxybenzophenone; p-hydroxypropiophenone; 2,4-dihydroxybenzophenone; 1,1-is(4-hydroxy-3-methylphenyl)-cyclohexane; 1,1-bis(4-hydroxyphenyl)cyclohexane; salicylanilide; 4-hydroxy-2-methylaoetophenone; 2-acetylbenzoic acid; m-hydroxyacetanilide; p-hydroxyacetanilide; 2,4-dihydroxyacetophenone; 4-hydroxy-4′-methylbenzophenone; 4,4′-dihydroxybenzophenone; 2,2-bis-(4-hydroxyphenyl)-4-methylpentane; benzyl 4-hydroxyphenyl ketone; 2,2-bis(4-hydroxyphenyl)-5-methylhexane; ethyl-4,4-bis(4-hydroxyphenyl)-pentanoate; n-propyl-4,4-bis(4-hydroxyphenyl)pentanoate; isopropyl-4,4-bis(4-hydroxyphenyl)pentanoate; methyl-4,4-bis(4-hydroxyphenyl)pentanoate; 3,3-bis(4-hydroxyphenyl)-pentane; 4,4-bis(4-hydroxyphenyl)-heptane; 2,2-bis(4-hydroxyphenyl)1-phenylpropane; 2,2-bis(4-hydroxyphenyl)butane; 2,2′-methylene-bis(4-ethyl-6-tertiarybutyl phenol); 4-hydroxycoumarin; 7-hydroxy-4-methylcoumarin; 2,2′-methylenebis(4-octyl phenol); 4,4′-sulfonyldiphenol; 4,4′-thiobis(6-tertiarybutyl-m-cresol); methyl-p-hydroxybenzoate; n-propylp-hydroxybenzoate; benzyl-p-hydroxybenzoate. Preferred among these are the phenolic developer compounds. More preferred among the phenol compounds are 4,4′-isopropylidinediphenol; ethyl-4,4-bis(4-hydroxyphenyl)pentanoate; n-propyl-4,4-bis(4-hydroxyphenyl)pentanoate; isopropyl-4,4-bis(4-hydroxyphenyl)pentanoate; methyl-4,4-bis(4-hydroxyphenyl)pentanoate; 2,2-bis(4-hydroxyphenyl)-4-methylpentane; p-hydroxybenzophenone; 2,4-dihydroxybenzophenone; and 1,1-bis(4-hydroxyphenyl)cyclohexane. Acid compounds of other kinds and types are eligible. Examples of such other compounds are phenolic resins which are the product of reaction between, for example, formaldehyde and a phenol such as an alkylphenol, e.g., p-octylphenol, or other phenols such as p-phenylphenol, and the like; and acid mineral materials including colloidal silica, kaolin, bentonite, attapulgite, hallosyte, and the like.

Chromogenic organic solvent detectors also typically include a support or substrate as part of the overall composite. The support or substrate material is typically in sheet form. For purposes of this invention, sheets also mean webs, ribbons, tapes, belts, films, cards and the like. The substrate or support material can be opaque, transparent or translucent and could, itself, be colored or not. The substrate can be fibrous including, for example, paper and filamentous synthetic materials. It can be a film including, for example, cellophane and synthetic polymeric sheets cast, extruded, or otherwise formed.

The thickness of the substrate material is generally on the order of about 50–100 μm. The thickness may, however, be varied as desired without substantially affecting the method of the present invention.

The components of the color-forming system are in a contiguous relationship, substantially homogeneously distributed throughout the material deposited on the substrate. In manufacturing the detector, a coating composition may be prepared which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as Carnuba wax; synthetic waxes; lubricants such as zinc stearate; wetting agents and defoamers.

The color-forming system components are substantially insoluble in the dispersion vehicle (preferably water) and are ground to an individual average particle size of between about 1 micron to about 10 microns, preferably about 3 microns. The preferred polymeric binder means is substantially vehicle soluble although latexes are also eligible in some instances. Preferred water soluble binders include polyvinyl alcohol, hydroxy ethylcellulose, methylcellulose, methyl-hydroxy-propylcellulose, starch, modified starches, gelatin and the like. Eligible latex materials include polyacrylates, polyvinylacetates, polystyrene, and the like. The polymeric binder is also used to protect the coated materials from brushing and handling forces occasioned by storage and use of the thermal sheets. Binder should be present in an amount to afford such protection and in an amount less than will interfere with achieving reactive contact between color-forming reactive materials.

As indicated above, the method of the invention provides a quick, easy and inexpensive method of detecting and mapping contamination of a surface by an organic solvent or organic solvent-containing material. Additionally, the present method may also be used to test a surface which has been coated with an organic solvent-containing material for adequate drying, curing and/or adherence of the organic solvent-containing material to the surface.

In a preferred embodiment of the invention, the present method is used to detect whether a residual organic solvent-containing material such as an electrolyte has remained on a surface from which the organic solvent-containing material was to be removed. In this way, it is possible to quickly, simply and reliably test various release materials to determine which materials provide the smallest degree of adherence, i.e., the material which has the most effective release properties.

According to the preferred embodiment of the invention, the surface of a release material which was previously in contact with an organic solvent-containing material is contacted with a suitable thermal paper. The thermal paper is then analyzed to determine the location and extent to which the organic solvent-containing material adhered to the surface of the release material. A suitable thermal paper is one that develops a noticeably darker color when contacted directly or indirectly with the organic solvent. Hewlett-Packard Corporation is a known supplier of a thermal paper suitable for the detection of ketone.

In order to further illustrate the present invention and the advantages thereof, the following specific examples are given, it being understood that the same are intended as illustrative and in no way limiting.

EXAMPLES

Introduction

Historically, in the manufacture of solid polymeric electrolytes, Mylar polyester film was used for covering cured solid electrolyte on laminates. When the Mylar film was peeled off the laminate after a few days of storage, part of the electrolyte often adhered to the Mylar film. This work was an attempt to find a material with good release property for the cured electrolyte.

EXAMPLE 1

A piece of solid electrolytic cell laminate was covered with silicone-coated Mylar. The covered laminate was vacuum sealed in bags and stored at room temperature for 46 hours. The bag was cut open and the Mylar was peeled off the laminate. In some areas, electrolyte peeled off the cathode and adhered to the Mylar film. Some liquid also adhered to the Mylar film.

The Mylar film was pressed against a piece of filter paper and rolled with a wooden roller. By rolling the filter paper against the Mylar, the electrolyte was transferred to the filter paper and no longer adhered to the Mylar.

The filter paper was pressed against a sheet of thermal paper for approximately 30 seconds. When the filter was removed, there appeared an image developed on the thermal paper roughly corresponding to the distribution of the electrolyte on Mylar. Some darkened area did not correspond to areas of cured electrolyte on Mylar, but corresponded to extraneous liquids on the Mylar.

To discriminate against the showing of the area with extraneous liquid, the filter paper was air dried at room temperature for about an hour. During this period, most of the liquid spread out and evaporated. The image that developed was free from the interference of extraneous liquids on Mylar, and only showed the area with cured electrolyte on Mylar.

A similar method could be used to detect and map organic solvents on a surface. A more sensitive method would be to press the surface directly against thermal paper.

EXAMPLE 2

Introduction

In this example, nine polymer release films were tested as electrolyte cover sheets. The choices of the nine polymer films were based mainly on contact angles.

Experimental

The materials tested were:

| Code | Supplier | Product | Type |
| --- | --- | --- | --- |
| A | Akrosil | 31582000 | silicone |
| B | Akrosil | 31502400 | silicone |
| C | Akrosil | 31003400 | silicone |
| D | Release Tech | 3-HID-M23B-Nat | thermally cured silicone |
| E | Release Tech | 1.5-HiD-ST3A-Blue | E beam cured silicone |
| F | Johnson Laminating | PET "easy release" 142 ga | silicone |
| G | Du Pont Electronics | 100 A | Teflon FEP |
| H | Valence Denmark | Terfilm E | poly propylene |
| I | Georgia Pacific | HB-T-1, 1 mil | hi density polyethylene |

Fresh cathode/electrolyte laminates were covered with polymer film. The covered laminate pieces were vacuum sealed in bags. Peel tests were conducted after 6, 24, 54, 96, 150 and 216 hours of storage at room temperature. The method of testing these materials was as described in Example 1, above.

Results

A dark area indicates electrolyte adhering to the cover sheet. Where no image was seen, there was no electrolyte adhering. The results showed that Akrosil 31582000, Release Tech 3-HID-23B-Nat, Johnson laminating PET easy release and Du Pont Electronics 100A performed satisfactorily as release materials.

While the invention has been described in terms of various preferred embodiments, the skilled artisan will appreciate that various modifications, substitutions, omissions, and changes may be made without departing from the spirit thereof.

We claim:

1. A method for detecting and mapping organic solvent-containing materials on a surface using a chromogenic solvent detector which comprises:
   a substrate;
   a binder means which is substantially soluble to said solvent;
   an electron donating chromogenic composition dispersed on said substrate in connection with said binder means; and
   an electron accepting composition, which forms a color with said chromogenic composition, dispersed on said substrate in connection with said binder means,
   said method comprising the steps of contacting said surface with said detector, dissolving said binder means of said detector in a region of contact with said organic solvent-containing material with said organic solvent-containing material, and detecting a visual discoloration of said detector caused by the contact of said organic solvent-containing material with said detector.

2. The method of claim 1, wherein said surface is directly contacted with said chromogenic solvent detector.

3. The method of claim 1, wherein said surface is indirectly contacted with said chromogenic solvent detector.

4. The method of claim 3, wherein said indirect contact comprises transferring said solvent-containing materials to said chromogenic solvent detector with an inert transfer means.

5. The method of claim 4, wherein said inert transfer means comprises filter paper.

6. The method of claim 4, wherein said inert transfer means comprises a first inert transfer means in direct contact with said surface to transfer the organic solvent-containing material to said detector and a second inert transfer means used to withdraw extraneous materials from said first inert transfer means.

7. The method of claim 6, wherein said first inert transfer means comprises a microporous material, and wherein said second inert transfer means comprises filter paper.

8. The method of claim 1, wherein said surface comprises a film of release material.

9. The method of claim 1, wherein said organic solvent-containing material comprises at least one polar solvent having a dielectric constant greater than about 8.

10. The method of claim 9, wherein said polar solvent has a dielectric constant greater than about 12.

11. The method of claim 10, wherein said polar solvent has a dielectric constant greater than about 16.

12. The method of claim 9, wherein said polar solvent is selected from the group consisting of alcohol, glycol, polyol, aldehyde, carbonate, acetone, ester, ether, ketone, dimethylsulfoxide, dioxolane, sulfolane, butyrolactone, and tetrahydrofuran.

13. The method of claim 12, wherein said alcohol contains less than about 8 carbon atoms.

14. The method of claim 12, wherein said ketone contains less than about 6 carbon atoms.

15. The method of claim 12, wherein said esters contains less than about 8 carbon atoms.

16. The method of claim 1, wherein said organic solvent-containing material comprises an electrolyte.

17. The method of claim 1, wherein said detector comprises at least one electron donating dye precursor and at least one electron accepting compound.

18. The method of claim 12, wherein said detector consists of thermal paper.

19. A method of testing the release properties of a release material comprising contacting a surface which was previously in contact with an organic solvent-containing material and detecting the presence of an organic solvent adhered to said surface by the method according to claim 1.

* * * * *